United States Patent [19]
Huang et al.

[11] Patent Number: 5,133,713
[45] Date of Patent: Jul. 28, 1992

[54] APPARATUS OF A SPINNING TYPE OF RESECTOSCOPE FOR PROSTATECTOMY

[76] Inventors: Jong-Khing Huang, Department of Surgery/Urology, Veterans General Hospital, Shihpai; W. H. Chen, 10F, No. 586, Tun-Hwa S. Rd., Taipei; Robert Y. S. Wang, P.O. Box 26-800, Taipei; Chau C. Chu, No. 10, Alley 9, Lane 696, Chung Ming S. Rd., Taichung, all of Taiwan

[21] Appl. No.: 501,724
[22] Filed: Mar. 30, 1990
[51] Int. Cl.⁵ ............................................. A61B 17/36
[52] U.S. Cl. ...................................... 606/46; 606/180
[58] Field of Search ................ 606/39, 40, 45, 46, 606/49, 180; 604/22; 128/751, 755

[56] References Cited

U.S. PATENT DOCUMENTS

| | | | |
|---|---|---|---|
| 2,448,741 | 9/1948 | Scott et al. | 606/46 |
| 2,484,059 | 10/1949 | Wallace | 606/46 |
| 2,487,502 | 11/1949 | Willinsky | 606/46 |
| 3,149,633 | 9/1964 | Zingale | 606/46 |
| 3,955,578 | 5/1976 | Chamness et al. | 606/47 |
| 4,068,667 | 1/1978 | Iglesias | 606/46 |
| 4,311,144 | 1/1982 | Harada | 606/46 |
| 4,345,599 | 8/1982 | McCarrell | 606/113 |
| 4,461,305 | 7/1984 | Cibley | 606/113 |
| 4,651,280 | 3/1987 | Chang et al. | 364/413 |
| 4,657,018 | 4/1987 | Hakky | 606/46 |
| 4,770,174 | 9/1988 | Luckman et al. | 606/180 X |

*Primary Examiner*—Max Hindenburg
*Attorney, Agent, or Firm*—Cushman, Darby & Cushman

[57] ABSTRACT

An apparatus of a new type of resectoscope for prostatectomy essentially comprising an electrical driving system which is connected to a replaceable high resistivity electrotome, or a screw thread cutting-knife, and a tube-electrode to achieve the spinning-type of resection for prostate or bladder tumor. A DC-motor and a transmission-gear set are mounted within a hand grip. Other devices, such as the resectoscope sheath, telescope universal electro-surgical unit, optical light source, and universal light guide cable may be connected to this apparatus. The resectoscope provides a high speed operation, safety, effectiveness, and convenience.

17 Claims, 3 Drawing Sheets

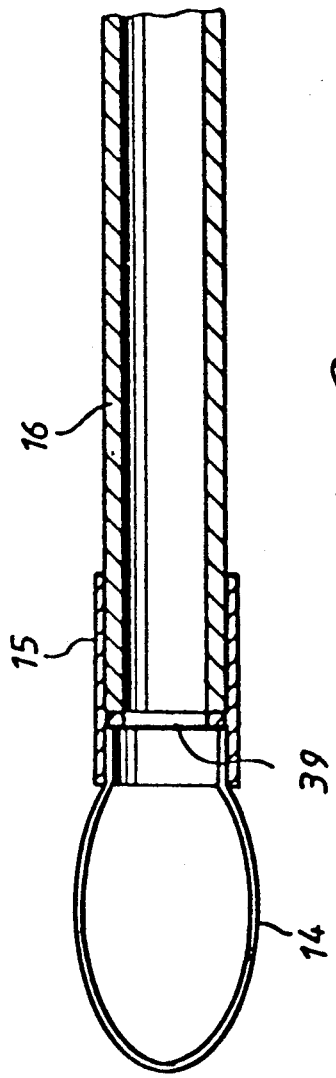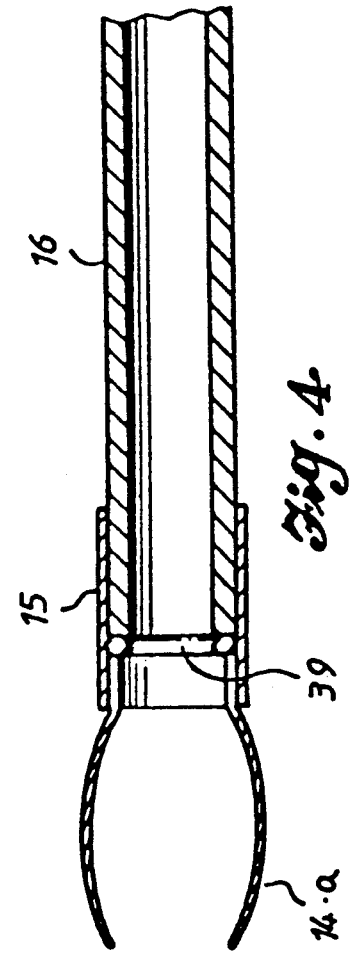

APPARATUS OF A SPINNING TYPE OF RESECTOSCOPE FOR PROSTATECTOMY

TECHNICAL FIELD

The present invention relates to an apparatus of a new type of resectoscope for prostatectomy. The main structure of this apparatus involves an electrical driving system which is connected to a replaceable high resistivity electrotome and a tube-electrode to achieve the spinning-type of resection for the prostate or bladder tumor. This resectoscope is different from other conventional devices and the spinning resecting process can reduce the operation time and the surgical complications of the patient, and increase the operating number of patients per unit time. The spinning type of resecting process requires only gentle translation and small angle wiggling of the resectoscope so that the effectiveness and safety are better than conventional devices.

BACKGROUND OF THE INVENTION

The conventional method of prostatectomy may be classified into the following four methods; the perineal prostatectomy, the suprapubic transvesical prostatectomy, the retropubic prostatectomy, and the transurethral resection of prostate which so-called TUR-P. Among these four methods, the last method is the only method which incorporates the endoscope. Nowadays, about 90% of the prostatectomy that are performed use the technique of transurethral method to resect the prostate, which is a well-known method.

The conventional device for the transurethral resection of prostate is a commercially available device which is a manual-type resectoscope in which the electrotome is made from a high resistivity metal wire, such as the tungsten wire or nickle-chrome alloy wire, with the electrotome having a semi-circular shape and perpendicular to the loop electrode. In operation, the electrotome is heated electrically by applying an electrical voltage across the wire which is used to resect the prostate. An operation performed using this device requires a mechanical scratch of the resectoscope to cut away the unwanted part of the tissue. This mechanical scratching process is controlled manually by the operator.

One of the disadvantages of this conventional device is that the operation is very slow because the mechanical scratching process is employed and the resecting process is a one-cut by one-cut process instead of a continuous cutting process. It usually takes at least half an hour for a skilled operator to finish an operation. Such a slow resection is certainly undesirable because it causes a long period of bleeding at the resecting portion and produces more complications for the patient, and also limits the operable number of patients in a given time interval. This leads to a high operation cost per resection.

Another disadvantage of this conventional device is that the scratching cutting process involves a large angle movement of the resectoscope, controlled by the hands of the operator and is therefore not precise and may potentially cut through the prostate capsule and external sphincter. This may lead to complications of capsule perforation and urination incontinence after the operation. The patient may need further operations or reconstructive procedures which may seriously injure the patient morally and physically.

SUMMARY OF THE INVENTION

The present invention relates to a new type of resectoscope for prostatectomy that is very different from that of the conventional devices. The conventional loop electrode has been replaced by an electrotome and a tube-electrode which is connected to a motor-driving transmission gear set so that the electrotome is spinnable. The electrotome is an oval electrode made from a high resistivity metal wire as a cutting loop and a wire holder, which is replaceable and exchangeable. The wire holder is inserted into an one end of the tube-electrode, and the other end of the tube-electrode is inserted into a specially designed electrical supply source via a spring contact and is connected to a gear set. The tube-electrode is a cylinder made from a good conductive metal with its inner and outer surfaces coated by a good insulating layer to ensure the electrical insulation. The conventional telescope is coaxially inserted into the tube-electrode to provide for interior observation during the resection of prostate. The hand held part of this apparatus is a hand grip with control buttons thereon, and a DC motor therein and a gear set to facilitate spinning of the electrotome.

It is the primary object of this invention to provide a method and apparatus to obtain a spinning type of resectoscope for prostatectomy which mitigates the disadvantages and limitations of the conventional device.

Another object of this invention is to provide a method and apparatus to obtain a spinning type of resectoscope for prostatectomy of which is motor-driving spinning resection. The spinning type of resectoscope can be fixed at the interior side of the verumontanum to cut the apex tissue of the prostate by the gentle and slow circular motion of the resectoscope, and prevent it from cutting through the external sphincter and the prostate capsule under the incorporation of the U.S. Pat. No. 4,651,280 "Electrosurgical control system using tissue conductivity". The apparatus of this invention provides a safer, faster, and more profitable transurethral resection of prostate.

A further object of this invention is to provide a method and apparatus to obtain a spinning type of resectoscope for prostatectomy which can speed-up the operation process, reduce operation time, reduce the bleeding of the patient, avoid complications that may be caused by the blood transfusion, and improve the safety and effectiveness of the operation.

Yet another object of this invention is to provide a method and apparatus to obtain a spinning type of resectoscope for prostatectomy, wherein the metal-wire type electrotome and the cutting loop are replaceable.

Still a further object of this invention is to provide a method and apparatus to obtain a spinning type of resectoscope for prostatectomy, wherein the hand-held part of the working element is equipped with push button switches that allow the selection of the cut mode or coagulation mode by using the fingers. The hand-held part of the working element is also different from that of the prior art device which has a mechanical push-pull mechanism on it to control in-and-out movement of the loop electrode, which is not necessary with the spinning type apparatus of this invention.

Still another object of this invention is to provide a method and apparatus to obtain a spinning type of resectoscope for prostatectomy which is compatible with the commercially available versatile electrosurgical generator.

Still a further object of this invention is to provide a method and apparatus to obtain a spinning type of resectoscope for prostatectomy which can be utilized with a robot for microcomputer-controlled electrotomy.

Other objects of this invention will become apparent as the description proceeds in connection with the accompanying drawings.

BRIEF DESCRIPTION OF THE DRAWINGS

Regarding drawings which illustrate embodiments of this invention.

FIGS. 3 and 4 are cross-sectional views of the electrotome in accordance with the present invention, which consists of an oval electrode and a short section of supporting tube. The oval electrode is made from a high resistivity metal wire and the electrotome is replaceable. The other type of oval electrode is an open loop type of cutting knife which is made from an annealed and hardened medium or high carbon steel. This knife, which is screw threaded in shape, can cut the prostate without applying any voltage.

DETAILED DESCRIPTION OF THE INVENTION

Figure 1:
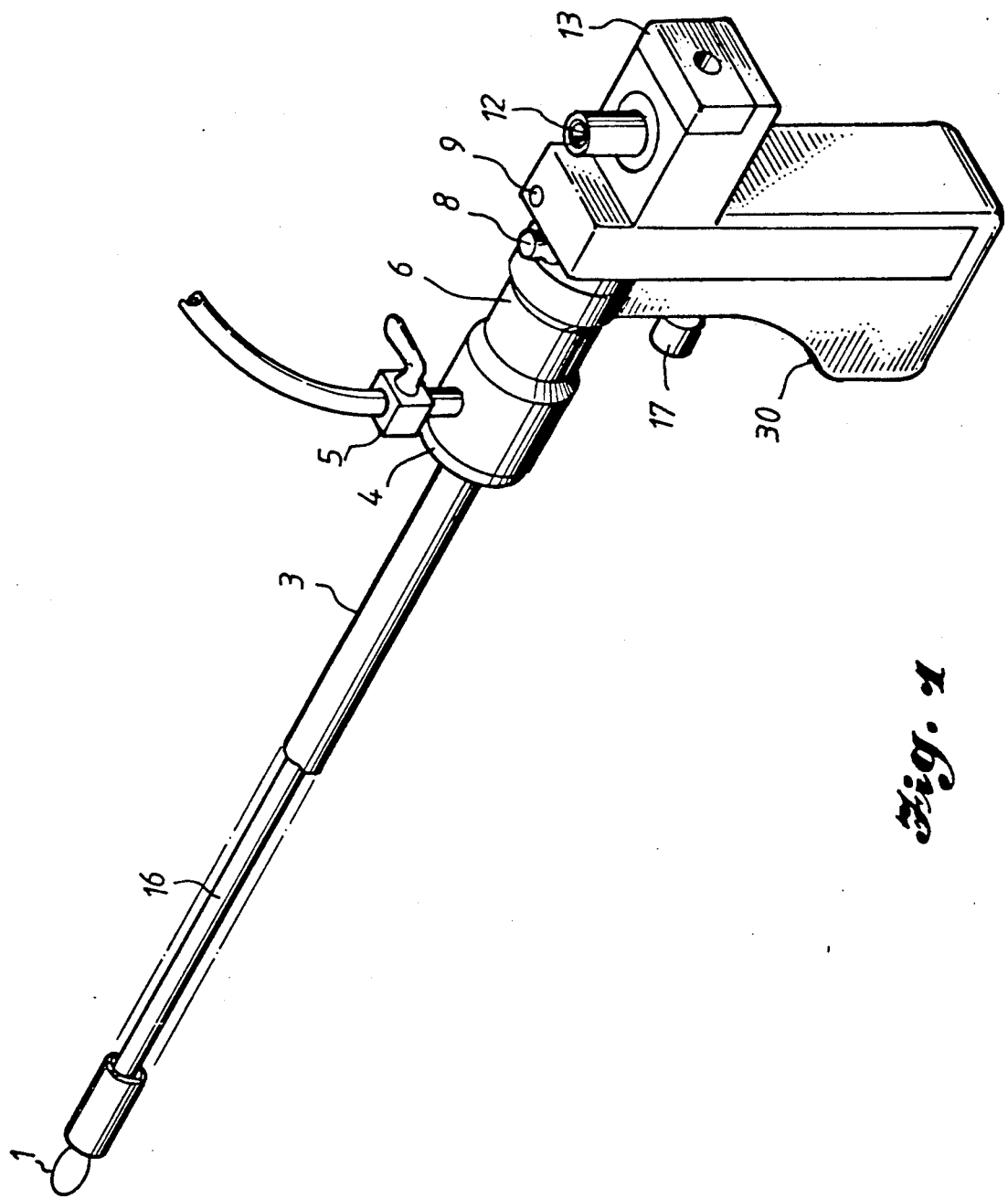
FIG. 1 is a perspective view of an apparatus of resectoscope for prostatectomy in accordance with the present invention.
Figure 2:
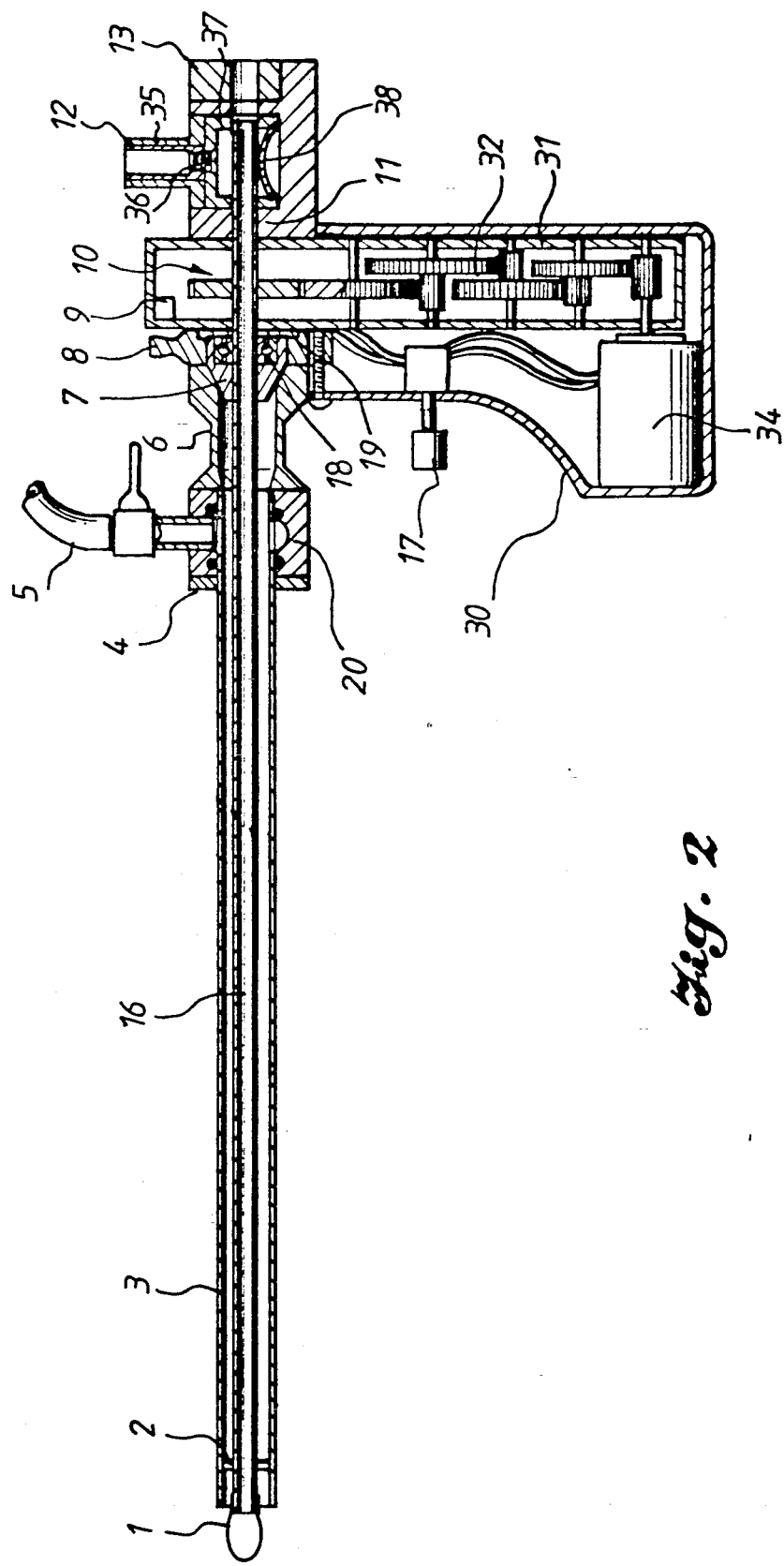
FIG. 2 is a cross-sectional view of the apparatus of a spinning type of resectoscope for prostatectomy in accordance with the present invention; it illustrates the tube-electrode which also provides a mechanical support and a rotational axis for the electrotome; it also shows the spring contact which allows the close contact of the tube electrode during its rotation.

Reference is now made to the Figures, where like reference numerals indicate corresponding parts. FIGS. 1 and 2 generally refer to the new type of resectoscope for prostatectomy in accordance with the present invention. As will become more apparent as the description proceeds, the resectoscope is a spinning type of device essentially comprising the following five parts: i.e., the resectoscope sheath, the working element, the telescope, the electrotome and tube electrode, and the transmission system. Besides these five parts, there are accessories, and some external equipment rendering the resectoscope operable. These accessories are commercially available, for example-the universal electro-surgical generator, the optical light source, the universal light guide cable, the electrical cord etc. This equipment is all compatible with the apparatus in accordance with the present invention.

The resectoscope sheath, as shown in FIG. 2 consists of an outer tube as the sheath 3, an inner tube (not shown), a locker 4, a stopcock 5, and a body 6. The inner tube is slightly longer than the outer tube and has a smooth head-end. In operation, the resectoscope sheath 3 is first inserted into the tissue at the beginning of the operation and acts as a guide-tube, then the inner tube is pulled out for the electrotome 1 and tube electrode 16 to coaxially sheathe into the prostate. The inner and outer surfaces of the front-end of outer tube 3 are coated with a layer of epoxy. A stabilizer 2 is located at the front-end of the tube electrode 16 to ensure stable rotation of the tube electrode 16. The stopcock 5 is connected to the body 6 and fixed by the locker 4.

The stopcock 5 is connected to a water supply by a hose to clean-up the resected tissue in the prostate and facilitate observation of the interior resecting portion through a telescope. The sheath 3 has the locker 4 to lock or unlock from the body 6.

The working element which is the major part of this invention consists of an electrotome 1, the tube electrode 16, a stop valve 7, a locking mechanism 8, an electrical adaptor for motor 9, a transmission system 10, an input power seat 11, a connector for the electrical cord 12, an adaptor for the telescope 13, and a hand grip 30.

The electrotome 1, as shown in FIG. 1 and FIG. 3, is an oval loop of metal-wire 14 that serves as a cutting loop and a short section of cylindrical tube 15 that serves as a cutting loop holder and is used to support the oval loop 14. The oval loop 14 is made from a high resistivity metal wire, such as tungsten wire or nickle-chrome alloy wire or nickle-chrome alloy wire. The cutting loop holder 15 is a highly conductive metallic tube. The electrotome 1 is inserted into the one end of the tube electrode 16. The other end of the tube electrode 16 is connected to the transmission gear set 32 and an input power seat 11, which is connected to a universal electro-surgical unit through the connector 12 and an electrical cord. In operation, the high voltage is applied to heat the electrotome 1 for resection or for coagulation. The cutting loop can also be a pure mechanical cutting knife 14-a, which is shown in FIG. 4. This cutting knife 14-a is an open elliptic loop which has a screw thread cutting curve. The cutting knife 14-a is made from an annealed and hardened medium steel or high carbon steel which is screw threaded in shape. The cutting knife 14-a can be used for resection with no external voltage, and can also be used for coagulation if high voltage is applied.

The electrotome 1 in accordance with the present invention is replaceable and exchangeable. The electrotome 1 is spinnable by the motor-derived transmission gear set 32 via the tube electrode 16. The inner and outer surfaces of the tube electrode 16 are coated with a high insulating Teflon layer to ensure excellent electrical insulation.

Referring to FIG. 2, a stop valve 7 is fixed onto the tube electrode 16 to stop water leakage and lock to the body 6. The locking mechanism 8, as shown in FIGS. 1 and 2, is used to lock and fix the hand grip 30 to the resectoscope sheath 3 via body 6. The transmission system 10 is located inside the hand grip 30. Reference numeral 31 is a gear box. The hand grip 30 is equipped with a button 17 to switch the motor on and off. Optionally, more buttons may be installed to select the electrical voltage for resection mode or coagulation mode for the electrotome 1. Within the gear box 31, a gear set 32 and a DC motor 34 are installed. The electrical supply is connected to the DC motor through the adaptor 9. The detail structure of the transmission system 10 can be seen in FIG. 2. The spinning speed of the electrotome 1 is variable by adjusting the gear set 32. The lateral cross-sectional view and top view of the detail structure of input power seat 11 are shown in FIG. 2 in which the reference numeral 38 is referred to a spring contact which is always kept in close contact with the tube electrode 16 when it rotates to supply the electrical voltage to the electrotome 1 through the tube electrode 16. Electrical connector 12 is fixed to spring contact holder 37 by using a copper bolt 36, and 35 is the insulating-protection cover for the connector 12.

Reference numeral 13 in FIGS. 1 and 2 is an adaptor for the telescope which is designed to match the telescope of the conventional device. Therefore, the conventional telescope of the device can be adopted directly to the resectoscope in accordance with the present invention. The telescope is inserted into the tube electrode 16 coaxially. The tube electrode 16 has a stabilizer 2 at the front end thereof, as shown in FIGS. 1 and 2, to ensure stable rotation of the electrode thereof. The spinning of the tube electrode 16 does not effect the viewing of the telescope. In the resectoscope of the present invention, a telescope may be adequate for resection, although other viewing angles of telescopes can still be used.

In operation, the electrical voltage generated from a universal electro-surgical unit is transmitted by a cord to the connector 12. Another electrical source connected to the adaptor 9 is used to drive the DC motor 34 and the transmission gear set 32 to spin the tube electrode 16 and the electrotome 1. The telescope has a connector connected to an optical light source generator using a light cable. The irrigating water is led into the prostate from a water source through the resectoscope sheath 3 and the stopcock 5.

This new type of resectoscope provides several important features such as safety, effectiveness, function ability, compatibility, and most importantly, it speeds up the operation.

The present invention has been described with respect only to an oval loop electrotome 1. This configuration or shape may or may not be valid, depending upon requirements. The electrotome 1 can be in the shape of 14-a, which is shown in FIG. 4 in which two pieces of medium-carbon steel or high-carbon steel are formed in the shape of a screw thread that can easily cut the tissue without applying any voltage through it.

Further variations and modifications may also be made without departing from what we regard as our invention. For example, the principles of our invention may be applied virtually to any embodiment described or suggested in the prior art devices, and current commercially available devices such as Olympus products, by substituting for its loop electrode and manual-type of working element our counterparts of the spinning mechanisms. All of the advantages described herein may then be obtained from such other embodiments. While the invention has been described and illustrated in detail, it should be clearly understood that this is intended by way of illustration and example only and should not to be taken in any way as a limitation. The spirit and scope of this invention are limited only by the terms of the following claims:

We claim:

1. A spinning type of resectoscope for prostatectomy, comprising:
    power transmission means for transmitting rotational motion;
    a motor, operatively engaged with said power transmission means;
    a resectoscope sheath including an outer tube having a first and a second end with fluid supply means communicating to an interior thereof proximate said outer tube first end;
    a tube electrode, having both an inner and an outer surface, housed coaxially inside said outer tube so as to define an annular space therebetween, said tube electrode being operatively engaged with said power transmission means, proximate said first end, so as to allow said tube electrode to rotate relative to said resectoscope sheath when said motor is activated;
    rotary cutting means attached to an end of said tube electrode proximate said outer tube second end and extending in a direction away from said outer tube first end so as to extend beyond said outer tube, a first power source being electrically connected to said rotary cutting means by said tube electrode; and
    a hand grip enclosing said motor and power transmission means and containing a switch operatively connected to said motor so as to control an on/off state of said motor, a second electrical power source being electrically connected to said motor;
    wherein said tube electrode inner surface is coated with teflon and said tube electrode outer surface is wrapped with a plastic shrinkage tube.

2. An apparatus as claimed in claim 1, wherein said rotary cutting means is an electrotome that is heated by said first power source for one of resection and coagulation processes.

3. An apparatus as claimed in claim 2, wherein said electrotome includes an oval loop of metal wire.

4. An apparatus as claimed in claim 3, wherein said metal wire is constructed of one of tungsten or a nickel-chrome alloy.

5. An apparatus as claimed in claim 1, wherein said rotary cutting means is a mechanical cutting knife that can be utilized for resection without receiving power from said first electrical power source and may be utilized for coagulation when receiving power from said first electrical power source.

6. An apparatus as claimed in claim 5, wherein said mechanical knife includes metal protrusions each having screw thread cutting surfaces.

7. An apparatus as claimed in claim 6, wherein said metal protrusions are constructed of one of annealed hardened medium carbon steel or high carbon steel.

8. An apparatus as claimed in claim 1, further comprising:
    an epoxy coating applied to at least a portion of an outer surface of said outer tube and at least a portion of said inner surface of said outer tube.

9. An apparatus as claimed in claim 1, wherein said outer tube is constructed of a metallic material.

10. An apparatus as described in claim 1, further comprising:
    a optical telescope inserted coaxially through said tube electrode; and
    a stopcock connected between said fluid supply means and said outer tube so as to allow for control of a fluid flowing through said annular space defined by said tube electrode and said outer tube to clean up resected tissue and facilitate observation of a resected portion through said telescope.

11. An apparatus as claimed in claim 1, wherein said resectoscope sheath is removably attached to said hand-grip.

12. An apparatus as claimed in claim 1, wherein said tube electrode is a metallic cylinder.

13. An apparatus as claimed in claim 1, further comprising:
    at least one stabilizer extending through at least a portion of said annular space, defined by said outer tube and said tube electrode, so as to ensure coaxial rotation of said tube electrode in said outer tube.

14. An apparatus as claimed in claim 1, wherein said tube electrode is electrically connected to said first power source by a rotatable contact proximate said first end.

15. An apparatus as claimed in claim 1, further comprising:
   a fluid tight seal between said tube electrode and said hand grip.

16. An apparatus as claimed in claim 1, wherein said power transmission means is variable so as to allow for different rotational speeds of said rotary cutting means.

17. A spinning type of resectoscope for prostatectomy, comprising:
   a power transmission means for transmitting rotational motion;
   a motor, operatively engaged with said power transmission means;
   a hand grip enclosing said motor and power transmission means;
   a resectoscope sheath disengageably mounted to said handgrip, said sheath having a first and a second end;
   a tube electrode mounted to said handgrip and being operatively engaged with said power transmission means proximate said sheath first end, said tube electrode being adapted to be inserted coaxially within said sheath so as to define an annular space therebetween;
   rotary cutting means;
   a cutting loop holder disposed between and connected to said cutting means and said tube electrode proximate said sheath second end, said cutting means extending away form said sheath first end so as to extend outside of said sheath whenever said tube electrode is inserted within said sheath; and
   a first power source electrically connected to said rotary cutting means by said tube electrode and said cutting loop holder,
   wherein said hand grip further includes a switch operatively connected to said motor so as to control an on/off state of said motor and a second electrical power source electrically connected to said motor.

* * * * *